US012788349B2

(12) United States Patent
Jia et al.

(10) Patent No.: US 12,788,349 B2
(45) Date of Patent: Nov. 10, 2026

(54) X-RAY IMAGING SYSTEM AND X-RAY IMAGING METHOD

(71) Applicant: GE Precision Healthcare LLC, Waukesha, WI (US)

(72) Inventors: Wencheng Jia, Beijing (CN); Lingzhi Zhou, Beijing (CN); Youbao Cao, Beijing (CN); Fusheng Li, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 106 days.

(21) Appl. No.: 18/933,790

(22) Filed: Oct. 31, 2024

(65) Prior Publication Data

US 2026/0114833 A1 Apr. 30, 2026

(30) Foreign Application Priority Data

Nov. 1, 2023 (CN) ......................... 202311444301.9

(51) Int. Cl.
*A61B 6/00* (2024.01)

(52) U.S. Cl.
CPC .......... *A61B 6/5241* (2013.01); *A61B 6/4452* (2013.01)

(58) Field of Classification Search
CPC .................................................. A61B 6/5241
See application file for complete search history.

(56) References Cited

U.S. PATENT DOCUMENTS

| | | | | |
|---|---|---|---|---|
| 9,986,954 | B2 | 6/2018 | Bailey | |
| 2011/0064193 | A1* | 3/2011 | Minnigh | A61B 6/505 378/98.12 |
| 2013/0114790 | A1* | 5/2013 | Fabrizio | A61B 6/5241 378/189 |
| 2015/0146851 | A1* | 5/2015 | Wilson | A61B 6/505 378/62 |
| 2016/0361035 | A1* | 12/2016 | Lee | A61B 6/469 |
| 2022/0414825 | A1* | 12/2022 | Hsu | G06T 7/337 |

* cited by examiner

*Primary Examiner* — Chih-Cheng Kao

(57) ABSTRACT

Provided in the present application are an X-ray imaging system and an X-ray imaging method. The X-ray imaging system includes an examination table, an X-ray source, and a controller. A detector is mounted inside the examination table, and the detector can carry out motion along the length direction and the width direction of the examination table. The X-ray source and the detector can cooperate to acquire an X-ray image of a subject under examination. The controller can control motion of the X-ray source and the detector to acquire a first quantity of X-ray images of the subject under examination along the width direction of the examination table, and can perform image stitching on the first quantity of X-ray images to acquire a panoramic image of the subject under examination in the width direction.

20 Claims, 8 Drawing Sheets

X-RAY IMAGING SYSTEM AND X-RAY IMAGING METHOD

CROSS-REFERENCE TO RELATED APPLICATIONS

This application is based on and claims priority to Chinese Application No. 202311444301.9, filed on Nov. 1, 2023, the entire contents of which is herein incorporated by reference.

TECHNICAL FIELD

The present invention relates to medical imaging technologies, and more specifically to an X-ray imaging system and an X-ray imaging method.

BACKGROUND

In an X-ray imaging system, radiation from an X-ray source is emitted toward a subject, and the subject under examination is usually a patient in a medical diagnosis application. Some of the radiation passes through the subject under examination and impacts a detector, which is divided into a matrix of discrete elements (e.g., pixels). The detector elements are read to generate an output signal on the basis of the amount or intensity of radiation that impacts each pixel region. The signal can then be processed to generate a medical image that can be displayed for review, and the medical image can be displayed in a display apparatus of the X-ray imaging system.

In a scanning process, there is occasionally a need for lateral (width-wise in terms of a human body) comparison of certain organs or sites, for example, it is sometimes necessary to compare images of the shoulders and neck on both sides of a subject under examination. However, for a subject under examination with a large body habitus or for conjoined subjects, it is challenging to capture both the left and right shoulders and neck in a single image, complicating lateral comparison for the subject(s) under examination.

SUMMARY

Provided in the present invention are an X-ray imaging system and an X-ray imaging method.

The exemplary embodiments of the present invention further provide an X-ray imaging system. The X-ray imaging system includes an examination table, an X-ray source, and a controller. A detector is mounted inside the examination table, and the detector can carry out motion along the length direction and the width direction of the examination table. The X-ray source and the detector can cooperate to acquire an X-ray image of a subject under examination. The controller can control motion of the X-ray source and the detector to acquire a first quantity of X-ray images of the subject under examination along the width direction of the examination table, and can perform image stitching on the first quantity of X-ray images to acquire a panoramic image of the subject under examination in the width direction.

The exemplary embodiments of the present invention further provide an X-ray imaging method. The X-ray imaging method includes: moving or rotating an X-ray source to a first position through an $n^{th}$ position along the width direction of an examination table, so as to acquire a first X-ray image to an $n^{th}$ X-ray image of a subject under examination; and stitching the first X-ray image to the $n^{th}$ X-ray image to acquire a panoramic image of the subject under examination in the width direction, where n is a first quantity.

The exemplary embodiments of the present invention further provide an X-ray imaging method. The X-ray imaging method includes: moving or rotating an X-ray source along the width direction of an examination table to acquire a first quantity of X-ray images; performing image stitching on the first quantity of X-ray images to acquire a panoramic image of a subject under examination in the width direction; moving or rotating the X-ray source along the length direction of the examination table to acquire a second quantity of X-ray images; performing image stitching on the second quantity of X-ray images and the panoramic image to acquire a whole-body image of the subject under examination.

Other features and aspects will become apparent from the following detailed description, drawings, and claims.

BRIEF DESCRIPTION OF THE DRAWINGS

The present invention can be better understood by means of the description of the exemplary embodiments of the present invention in conjunction with the drawings, in which.

DETAILED DESCRIPTION

Specific embodiments of the present invention will be described below. It should be noted that in the specific description of said embodiments, for the sake of brevity and conciseness, the present description cannot describe all of the features of the actual embodiments in detail. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for those of ordinary skill in the art related to the content disclosed in the present invention, some design, manufacture, or production changes made on the basis of the technical content disclosed in the present disclosure are only common technical means, and should not be construed as the content of the present disclosure being insufficient.

Unless defined otherwise, technical terms or scientific terms used in the claims and description should have the usual meanings that are understood by those of ordinary skill in the technical field to which the present invention belongs. The terms "first" and "second" and similar terms used in the description and claims of the patent application of the present invention do not denote any order, quantity, or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Figure 1:
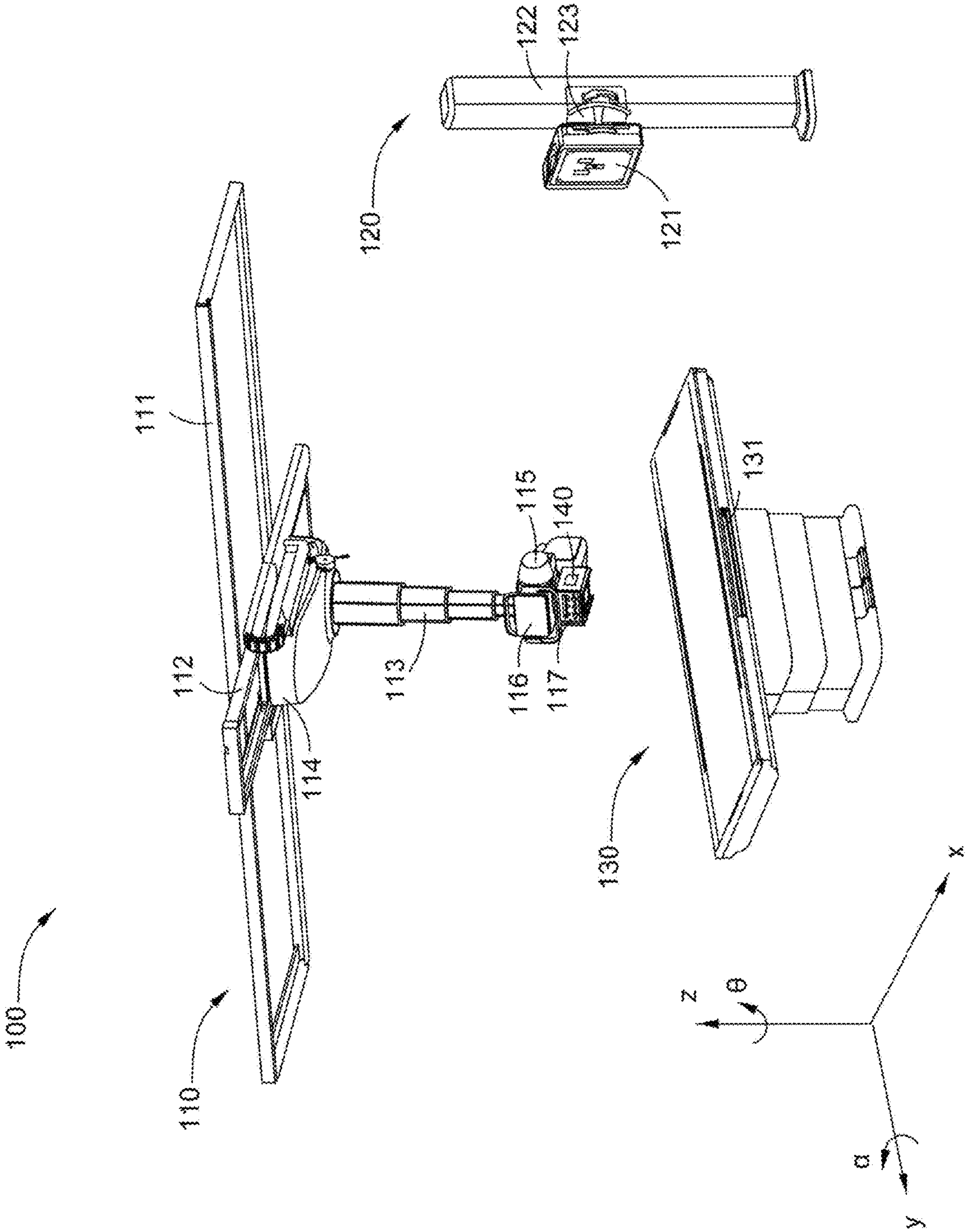
FIG. 1 is a schematic diagram of an X-ray imaging system according to some embodiments of the present invention.

FIG. 1 shows an X-ray imaging system 100 according to some embodiments of the present invention. As shown in FIG. 1, FIG. 1 shows the X-ray imaging system 100 according to some embodiments of the present invention. As shown in FIG. 1, the X-ray imaging system 100 includes a suspension apparatus 110, a wall stand apparatus 120, and an examination table 130. The suspension apparatus 110 includes a longitudinal guide rail 111, a transverse guide rail 112, a telescopic cylinder 113, a sliding member 114 and a tube assembly 115.

For ease of description, in the present application, the x-axis, y-axis, and z-axis are defined as the x-axis and y-axis being located in a horizontal plane and perpendicular to one another, and the z-axis being perpendicular to the horizontal plane. Specifically, a direction in which the longitudinal guide rail 111 is located is defined as the y-axis, a direction in which the transverse guide rail 112 is located is defined as the x-axis direction, and an extension direction of the telescopic cylinder 113 is defined as the z-axis direction, and the z-axis direction is the vertical direction.

The longitudinal guide rail 111 and the transverse guide rail 112 are perpendicularly arranged, the longitudinal guide rail 111 being mounted on a ceiling and the transverse guide rail 112 being mounted on the longitudinal guide rail 111. The telescopic cylinder 113 is configured to carry the tube assembly 115.

The sliding member 114 is provided between the transverse guide rail 112 and the telescopic cylinder 113. The sliding member 114 may include components such as a rotating shaft, a motor, and a reel. The motor can drive the reel to rotate around the rotating shaft, which in turn drives the telescopic cylinder 113 to move along the z-axis and/or slide relative to the transverse guide rail. The sliding member 114 is capable of sliding relative to the transverse guide rail 112, i.e., the sliding member 114 is capable of driving the telescopic cylinder 113 and/or the tube assembly 115 to move in the y-axis direction. Further, the transverse guide rail 112 can slide relative to the longitudinal guide rail 111, which in turn drives the telescopic cylinder 113 and/or the tube assembly 115 to move in the x-axis direction.

The telescopic cylinder 113 includes a plurality of cylinders having different inner diameters, and the plurality of cylinders can be sleeved, sequentially from bottom to top, into a cylinder located thereabove, thereby achieving telescoping, and the telescopic cylinder 113 can be telescopic (or movable) in the vertical direction, i.e., the telescopic cylinder 113 can drive the tube assembly to move along the z-axis direction. The lower end of the telescopic cylinder 113 is further provided with a rotating part, and the rotating part can drive the tube assembly 115 to rotate.

The tube assembly 115 includes an X-ray source, and the X-ray source may produce X-rays and project the X-rays to an intended region of interest (ROI) of a patient. Specifically, the X-ray source may be positioned adjacent to a beam limiter, and the beam limiter is used to align the X-rays with the intended region of interest of the patient. At least a part of the X-rays may be attenuated by means of the patient, and may be incident on a detector 121/131.

The suspension apparatus 110 further includes a beam limiter 117. The beam limiter 117 is usually mounted below the X-ray source, and the X-rays emitted by the X-ray source irradiate on the body of a subject under examination by means of an opening of the beam limiter 117. An irradiation range of the X-rays, namely the region size of an exposure field of view (FOV), depends on the size of the opening of the beam limiter 117. It is well known that X-rays are harmful to the human body, and it is thus necessary to control the X-rays, so that the X-rays only irradiate a site of the subject under examination that needs to be examined, i.e., the region of interest.

The suspension apparatus 110 further includes a tube console 116, the tube console 116 being mounted on the tube assembly. The tube console 116 includes user interfaces such as a display screen and a control button, used to perform preparation work before image capture, such as patient selection, protocol selection, positioning, etc.

Motion of the suspension apparatus 110 further includes rotation of the tube assembly 115 in a vertical plane and rotation of the tube assembly 115 in the horizontal plane. That is, when the tube assembly 115 rotates in the vertical plane, the tube assembly rotates around the y-axis, and an angle of rotation of the tube assembly 115 with respect to an initial position is defined as a first rotation angle $\alpha$. When the tube assembly 115 rotates in the horizontal plane, the tube assembly rotates around the z-axis, and an angle of rotation of the tube assembly 115 with respect to the initial position is defined as a second rotation angle $\theta$. For ease of illustration, a corrugated tube is omitted in FIG. 1.

In the above motion, a motor is usually used to drive a rotating shaft, which in turn drives corresponding components to rotate in order to achieve corresponding movement or rotation, and corresponding control components are generally mounted in the sliding member 114. An X-ray imaging unit further includes a motion control unit (not shown in the figures), and the motion control unit can control the described motion of the suspension apparatus 110. Furthermore, the motion control unit can receive a control signal to control a corresponding component to carry out motion correspondingly.

In some embodiments, the X-ray imaging system 100 further includes a camera unit 140, and the camera unit 140 is aligned with the detector so as to be configured to acquire a real-time camera image of the subject under examination. In addition, the camera is able to acquire an image of the detector, etc.

Specifically, the camera unit 140 is mounted on the suspension apparatus 110, and further, on a side of the beam limiter 117. The camera unit may include one or more cameras, for example, a digital camera, an analog camera, etc., or a depth camera, an infrared camera, or an ultraviolet camera, etc., or a 3D camera, a 3D scanner, etc., or a red, green, and blue (RGB) sensor, an RGB depth (RGB-D) sensor, or other devices that can capture color image data of a target subject. In some embodiments, the camera unit 140 is further provided with a control module that can control the rotation of the camera unit to adjust the capture range of the camera unit. In other embodiments, the camera unit is a panoramic camera that can take an image of the entire body of the subject under examination.

The camera unit 140 can acquire depth information or a depth image of the subject under examination. Typically, the depth information is calculated from a 3D point cloud that is acquired by the camera. In addition, the real-time camera image can be used to acquire at least one of the thickness, height, position, body position, pose, etc. of the subject under examination. In some embodiments, the camera unit 140 may also be a camera unit that is mounted in a fixed position, or fixed in any other way in a scan room. In some embodiments, the camera image acquired by the camera unit is not limited to a single camera image, but may also include a dynamic real-time video stream, i.e., a series of real-time camera images.

The wall stand apparatus 120 includes a first detector assembly 121, a wall stand 122, and a connecting portion 123. The connecting portion 123 includes a support arm that is vertically connected in the height direction of the wall stand 122 and a rotating bracket that is mounted on the support arm, and the first detector assembly 121 is mounted on the rotating bracket. The wall stand apparatus 120 further includes a detector driving apparatus that is arranged between the rotating bracket and the first detector assembly 121, which is driven by the detector driving apparatus to move in a direction parallel to the height direction of the wall stand 122 in the plane held by the rotating bracket, and the first detector assembly 121 can further be rotated relative to the support arm to form an angle with the wall stand. The first detector assembly 121 has a plate-like structure, the orientation of which is variable, facilitating an X-ray incident surface to become vertical or horizontal depending on the incident direction of the X-rays.

A second detector assembly 131 is included on the examination table 130, and the selection or use of the first detector assembly 121 and the second detector assembly 131 may be determined on the basis of an image capture site of a patient and/or an image capture protocol, or may be determined on the basis of a position of the subject under examination obtained by image capture of a camera, so as to perform image capture and examination in a lying or standing position. FIG. 1 only shows an example diagram of a wall stand and an examination table, and it should be understood by those skilled in the art that wall stands and/or examination tables of any form or arrangement can be selected, or only the wall stand can be mounted, and the wall stand and/or examination table is not intended to limit the overall solution of the present application.

The X-ray imaging system further includes a control apparatus (not shown in the figures), which may be a main control apparatus that is located in a control room, a tube console that is mounted on the suspension apparatus, a mobile or portable control apparatus, or any combination of the above. The control apparatus may include a source control apparatus and a detector control apparatus. The source control apparatus is used to command the X-ray source to emit X-rays for image exposure. The detector control apparatus is used to select a suitable detector among a plurality of detectors, and to coordinate the control of various detector functions, such as automatically selecting a corresponding detector according to the position or pose of the subject under examination. Alternatively, the detector control apparatus may perform various signal processing and filtering functions, specifically, for initial adjustment of a dynamic range, interleaving of digital image data, and the like. In some embodiments, the control apparatus may provide power and timing signals for controlling the operation of the X-ray source and the detector.

In some embodiments, the control apparatus may also be configured to use a digitized signal to reconstruct one or more required images and/or determine useful diagnostic information corresponding to a patient, and the control apparatus may include one or more dedicated processors, graphics processing units, digital signal processors, microcomputers, microcontrollers, application-specific integrated circuits (ASICs), field-programmable gate arrays (FPGAs), or other appropriate processing apparatuses.

Certainly, the X-ray imaging system may further include other numbers or configurations or forms of control apparatuses, for example, the control apparatus may be local (e.g., co-located with one or more X-ray imaging systems 100, e.g., within the same facility and/or the same local network). In other implementations, the control apparatus may be remote, and thus only accessible by means of a remote connection (for example, by means of the Internet or other available remote access technologies). In a specific implementation, the control apparatus may also be configured in a cloud-like means, and may be accessed and/or used in a means that is substantially similar to the means by which other cloud-based systems are accessed and used.

The X-ray imaging system 100 also includes a storage apparatus (not shown in the figures). The control apparatus may store the digitized signal in the storage apparatus. For example, the storage apparatus may include a hard disk drive, a floppy disk drive, a CD-read/write (CD-R/W) drive, a digital versatile disc (DVD) drive, a flash drive, and/or a solid-state storage apparatus. The storage apparatus is used to store a program that can be executed by a computer. Certainly, the storage apparatus may also be integrated with the control apparatus, so as to effectively use the footprint and/or meet expected imaging requirements.

In one embodiment, the X-ray imaging system 100 further includes an operator workstation, the operator workstation allowing the user to receive and evaluate the reconstructed image, and input a control instruction (an operation signal or a control signal). The operator workstation may include a user interface (or user input device) in a certain form of operator interface, such as a keyboard, a mouse, a voice activated control apparatus, or any other suitable input device, such that an operator may input an operation signal/control signal to the control apparatus by means of the user interface.

In a conventional X-ray imaging system, a second detector assembly in an examination table can be moved only along the length direction of the examination table. Existing image stitching can be performed only along the length (or height) direction of a human body. This is because the second detector assembly in the examination table can be moved only along the length direction of the examination table, and a first detector assembly in a wall stand can be moved only along the vertical direction (i.e., the standing direction of the human body). Limited by the moving direction of the detector assemblies, an exposure assembly can be moved only along the height direction of the human body to perform image stitching, and image stitching cannot be performed in the width direction of the human body to acquire a panoramic image in the width direction.

In addition, when a user or an operator needs to compare images of the user in the width direction, a subject under examination usually needs to move position, so that the left and right shoulders of the subject under examination are separately located at the position of the detector, and are exposed sequentially to acquire X-ray images of the left and right shoulders of the subject under examination. However, in a process in which the subject under examination moves for reposition, a posture of the subject under examination, angles between the shoulders and neck, etc. are all changed. Consequently, displacements or discrepancies are produced in the sequentially obtained images, causing a large error during the comparison.

For these problems, the applicant has proposed to acquire a plurality of X-ray images along the width direction of the examination table and then stitch the plurality of X-ray images to acquire a panoramic image of the subject under examination in the width direction, for example, a panoramic image of the shoulders and neck, on the basis that the detector assemblies in the examination table can be moved in the length direction and width direction.

Figure 2:
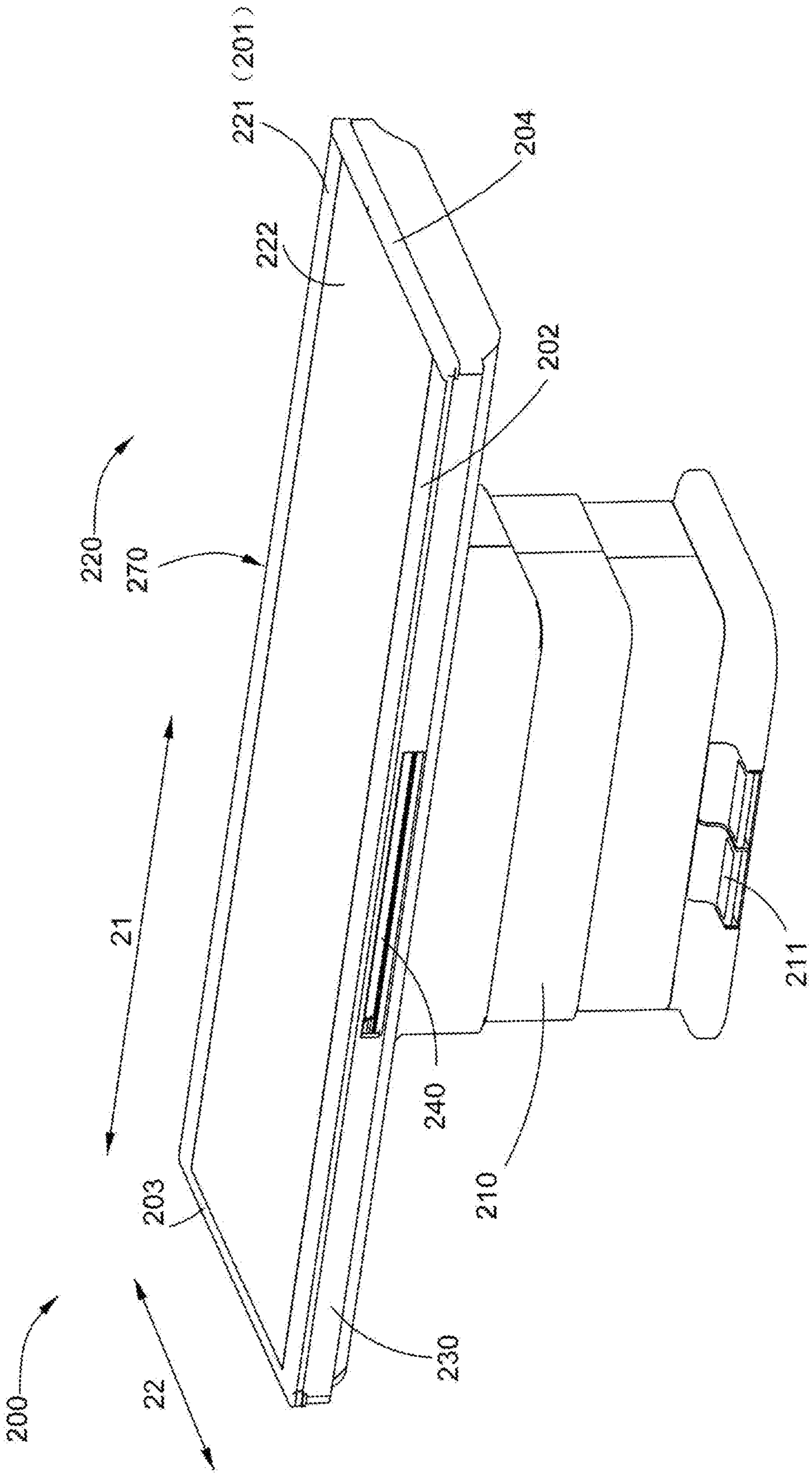
FIG. 2 is a schematic diagram of an examination table according to some embodiments of the present invention.
Figure 3:
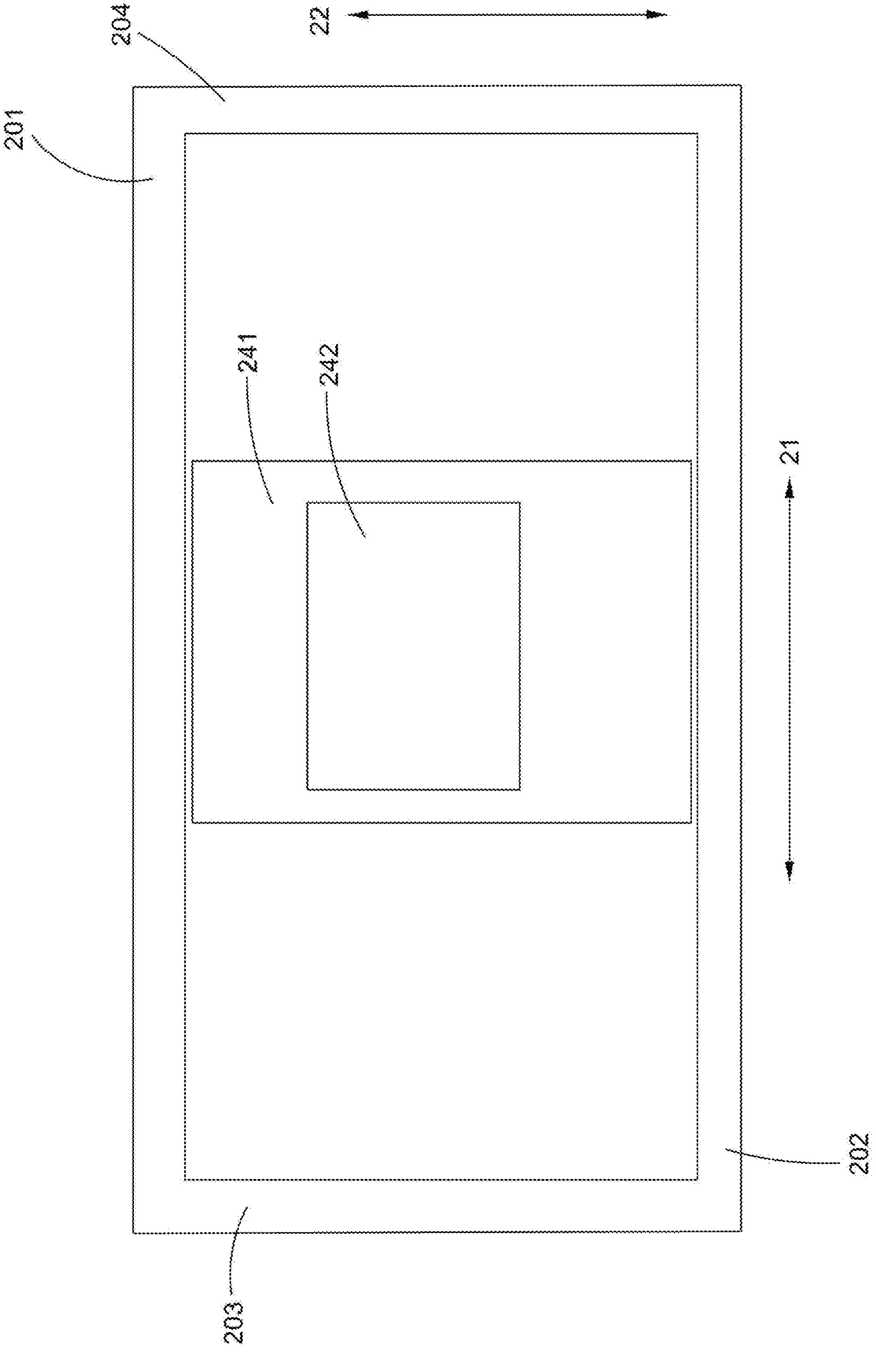
FIG. 3 is a schematic diagram of a detector according to some embodiments of the present invention.

FIG. 2 is a schematic diagram of an examination table 200 according to some embodiments of the present invention. FIG. 3 is a schematic diagram of a detector assembly according to some embodiments of the present invention. As shown in FIG. 2 to FIG. 3, the examination table 200 includes a base 210, a table panel assembly 220, a support assembly 230, and a detector assembly 240. For ease of description, a direction parallel to a long side of a table panel is referred to as the length direction 21 of the examination table, and a direction parallel to a short side of the table panel is referred to as the width direction 22 of the examination table.

Specifically, the table panel assembly 220 is mounted on the support assembly 230, and an accommodating space is present between the table panel assembly 220 and the support assembly 230. The accommodating space is used to accommodate the detector assembly 240. The detector assembly 240 is mounted on the support assembly 230, and the detector assembly 240 is movable along the length direction 21 and the width direction 22 relative to the support assembly 230. The support assembly 230 is mounted on the base 210.

In some embodiments, the base 210 has a generally rectangular-shaped, three-dimensional box-like structure, and the base 210 includes a plurality of housings that are sequentially sleeved. The plurality of housings may be sleeved, sequentially from bottom to top, in the housing located thereabove, thereby achieving telescoping so as to adjust the height of the examination table. In some embodiments, the examination table may further include a lifting assembly provided in the base 210. The support assembly 230 can be mounted on a top plate of the lifting assembly. The lifting assembly includes a lifting column and a motor, and power is supplied to the motor to raise or lower the lifting column so as to drive the support assembly to raise or lower the table panel assembly, but the embodiments of the present application are not limited thereto.

Specifically, the base 210 includes a pedal 211, and the pedal 211 can be used to control the height of the examination table, and the user can adjust the height of the examination table by means of controlling the pedal 211. It should be understood by those skilled in the art that the base may also be provided in any other form, for example, the base is provided so that the height cannot be adjusted or the height is adjusted in other forms, and the base is not limited to the above description.

The table panel assembly 220 includes a table panel frame 221 and a table panel 222. The table panel 222 is mounted on the table panel frame 221, and the table panel 222 is movably connected to the table panel frame 221. Specifically, the table panel frame 221 consists of four frames, internally forming a closed space. Specifically, the table panel frame 221 includes a first frame 201, a second frame 202 opposite the first frame 201, and a third frame 203 and a fourth frame 204 adjacent to the first frame 201, and the four frames are connected together by means of riveting, welding, key connection, or the like. Certainly, the table panel frame 221 may also be integrally molded. Specifically, the material of the table panel frame 221 is aluminum. Certainly, the table panel frame may also be made of other metal materials. The table panel 222 may be placed on the table panel frame 221, and certainly, may also be inserted in the table panel frame 221 so that an upper surface of the table panel and an upper surface of the table panel frame are in the same plane. Certainly, the table panel 222 may also be rotatably mounted in the table panel frame 221. For example, the first frame 201 of the table panel frame 221 and a side of the table panel 222 connected to each other form a rotating shaft 270, so that the table panel 222 can be opened inwards and outwards relative to the rotating shaft 270, and so on.

The table panel 222 may be made using a material having a lower X-ray attenuation, such as being composed of a carbon fiber composite material. The table panel 222 may include a one layer plate or a multilayer plate structure. For example, when the table panel 222 includes the multilayer plate structure, each layer uses a particular material, for example, an inner layer is made of foam and an outer layer is made of a material such as a carbon fiber composite material. Alternatively, a heating layer may be further added to the table panel 222, and heat generated by the heating layer is transferred to the outer layer in contact with the subject under examination. The material has an appropriate strength so as to provide stable support for a scanned object. For details, reference may be made to the prior art, which will not be described again here.

In some non-limiting embodiments, the rotating shaft 270 of the table panel frame 221 and the table panel 222 is arranged along the length direction 21 of the table panel. That is, the table panel can be flipped outward along the length direction, in other words, one long side of the table panel is fixed, and the other long side can be lifted or lowered. However, it should be understood by those skilled in the art that the rotating shaft may also be arranged in the width direction of the table panel, that is, the table panel can be flipped outward along the width direction.

The detector assembly 240 is mounted on the support assembly 230. The detector assembly 240 includes a tray 241 and a detector cartridge 242. A detector is provided or mounted in the detector cartridge 242. The detector has an X-ray receiving surface capable of receiving X-rays. The detector cartridge 242 is mounted or fixed on the tray 241.

In some embodiments, the detector assembly 240 includes a first group of moving assemblies for driving the detector cartridge 242 to move along the width direction 22. Specifically, the detector cartridge 242 can move from a side of the first frame 201 to a side of the second frame 202, and therefore, the receiving range of the detector cartridge 242 can be moved along the width direction 22 from one side of the table panel to another side.

Specifically, the first group of moving assemblies includes a first group of synchronous belts, a first group of guide rails, and a first motor. The first group of guide rails is arranged along the width direction 22. The bottom of the tray 241 is provided with guide rail slots opposite to the first group of guide rails, so that the tray 241 can move relative to the first group of guide rails. One end of the first group of synchronous belts is fixed on the tray 241, and the other end is connected to the first motor, so as to control the first group of synchronous belts by means of the first motor to drive the tray to carry out motion, so that the tray and the detector move along the width direction 22. Specifically, the first group of moving assemblies further includes at least one first group of sensors to feed back a position of the tray in the width direction.

Specifically, the detector assembly 240 further includes a second group of moving assemblies for driving the tray 241 to move the detector cartridge 242 along the length direction 21. Specifically, the detector assembly 240 can be moved from a side of the third frame 203 to a side of the fourth frame 204, and therefore, the receiving range of the detector cartridge 242 can be moved along the longitudinal axis from one side of the table panel to another side.

Specifically, the second group of moving assemblies includes a second group of synchronous belts, a second group of guide rails, and a second motor. The second group of guide rails is arranged along the length direction 21. The first group of guide rails is arranged on the second group of guide rails. The first group of guide rails is perpendicular to the second group of guide rails. The tray 241 can move relative to the second group of guide rails. One end of the second group of synchronous belts is fixed on the tray 241, and the other end is connected to the second motor, so as to control the second group of synchronous belts by means of the second motor to drive the tray to carry out motion, so that the tray and the detector move along the length direction 21. Specifically, the second group of moving assemblies further includes at least one second group of sensors to feed back a position of the tray in the length direction.

Figure 4:
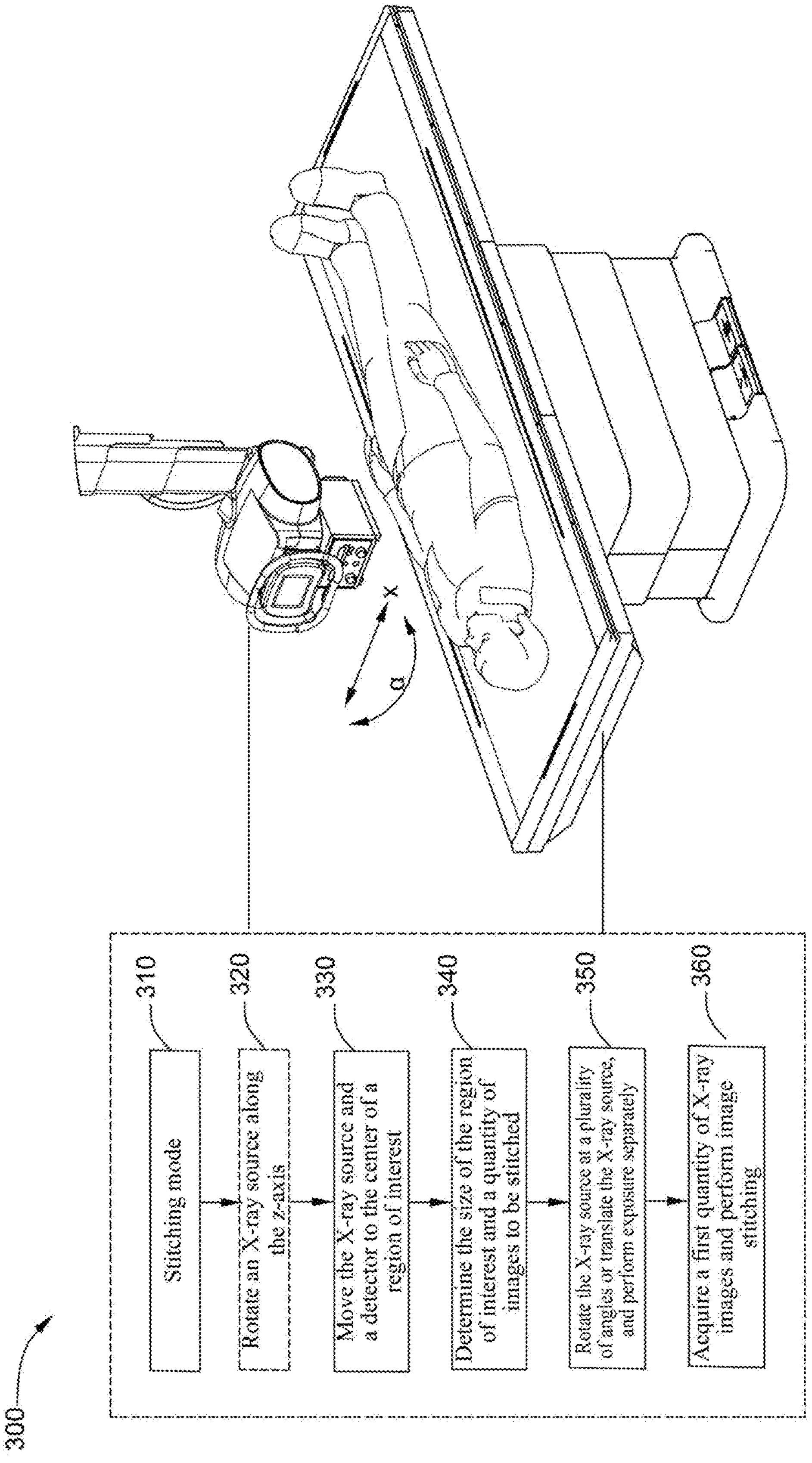
FIG. 4 is a schematic diagram of a region of interest according to some embodiments of the present invention.

FIG. 4 shows a schematic diagram of a control principle of a controller according to some embodiments of the present invention. As shown in FIG. 4, the controller can control motion of the X-ray source and the detector to acquire a first quantity of X-ray images of the subject under examination along the width direction of the examination table, and can perform image stitching on the first quantity of X-ray images to acquire a panoramic image of the subject under examination in the width direction.

The first quantity is an integer greater than 1. For example, two X-ray images may be acquired in the width direction and image stitching may be performed on the two X-ray images. Certainly, three X-ray images may be acquired and image stitching may be performed on the three X-ray images. Alternatively, there may be more images. Typically, how many X-ray images are captured in width depends on the width of an image capture site and the size of the detector.

Specifically, firstly, in 310, the controller can select or display a stitching mode based on a user's input. Specifically, the stitching mode includes a rotation mode and a translation mode. Specifically, a plurality of images to be stitched may be acquired by emitting X-rays at a plurality of different angles (or orientation positions), respectively, or a plurality of images to be stitched may be acquired by translating the X-ray source. This may be determined based on a user's or an operator's selection, or may be automatically determined based on an image capture site, or may be determined based on a default mode.

Secondly, optionally, in 320, when a selected stitching mode is the rotation mode, before images to be stitched are acquired by means of rotation, the controller can be further configured to control the X-ray source to rotate in the horizontal plane such that a reference line is parallel to the length direction of the examination table, where the reference line is a direction perpendicular to a screen plane of the tube console. Certainly, when a selected stitching mode is the translation mode, there is no need to rotate the X-ray source along the z-axis.

In the suspension apparatus, a default position of the tube console has the reference line aligned with the x-axis direction. Since the tube assembly needs to be controlled to rotate along the width direction of the examination table, the reference line of the suspension apparatus needs to be controlled to align with the y-axis direction, i.e., the tube assembly needs to be controlled to rotate by 90 degrees along the z-axis, so that the reference line is parallel to the length direction of the examination table. Such rotation arrangement enables the tube assembly to rotate along the width direction of the examination table. Certainly, if the tube assembly is already at a position that has the reference line aligned with the y-axis direction, the tube assembly does not need to be rotated along the z-axis, and the X-ray source is simply directly controlled to rotate, so as to acquire the images to be stitched.

Thirdly, in 330, the controller can be further configured to control the suspension apparatus to move such that the X-ray source and the detector are aligned with the center of a region of interest of the subject under examination. In some embodiments, for rotating the X-ray source along the z-axis in 320 and moving to the center of the region of interest in 330, control or motion may be synchronously carried out.

In some embodiments, the controller can automatically control the suspension apparatus to move to a target position (i.e., the center of the region of interest) by means of a position indicated by a handheld positioning apparatus.

Specifically, the handheld positioning apparatus includes at least one position detection unit, a signal transmission unit, and a trigger unit. The at least one position detection unit can emit detection signals towards a wall or a reflective plate in a room and receive reflected detection signals, and based on the emitted and received detection signals, calculate a target position of the handheld positioning apparatus in the room in which the scan room is located. The signal transmission unit is connected to the controller and transmits a current target position of the handheld positioning apparatus to the controller. The controller further controls the X-ray source and the detector to move to the target position based on the current target position. The trigger unit is configured to be connected to the signal transmission unit and control the signal transmission unit to transmit the current target position when the trigger unit is triggered.

A target position currently indicated by the handheld positioning apparatus is acquired in real time based on the detection signals transmitted and received by the position detection unit. This position is then transmitted to the controller via a trigger button. In this way, the controller can control the X-ray source and the detector to automatically move to the indicated target position. Additionally, by moving the position of the handheld positioning apparatus and through the controller wirelessly connected to the handheld positioning apparatus, the X-ray source and the detector can be moved to any intended target position.

Figure 5:
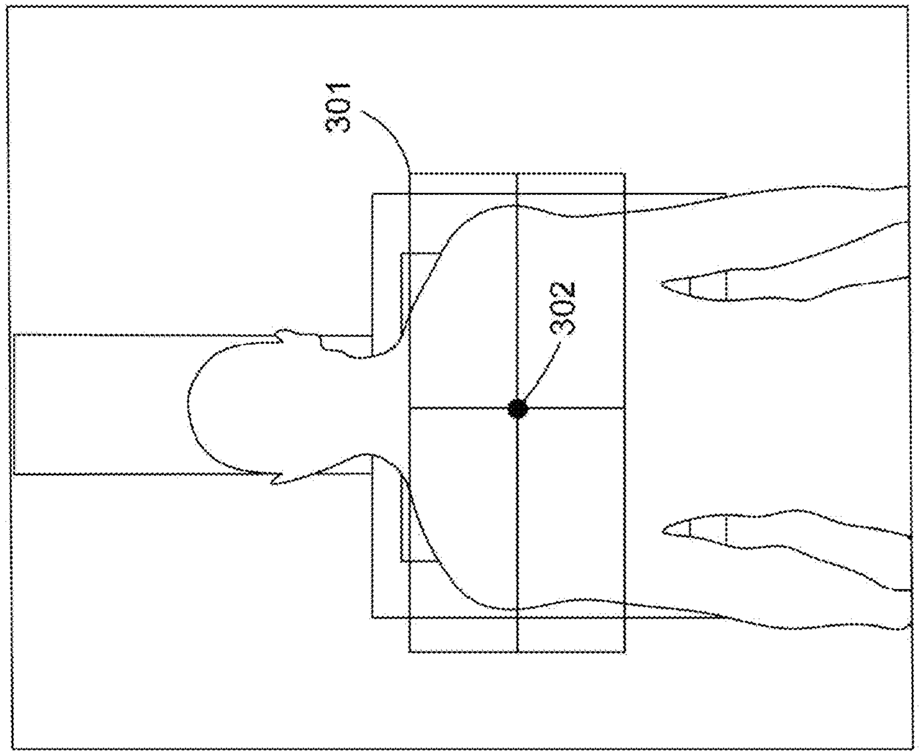
FIG. 5 is a schematic diagram of a control principle of a controller according to some embodiments of the present invention.

In some other embodiments, in a display interface of a camera image shown in FIG. 5, a position of the center 302 of the region of interest can be determined based on the camera image of the subject under examination. Then, a position of the center of an actual region of interest corresponding to the subject under examination can be determined based on a mounting position or angle or the like between the camera and the X-ray source. The controller then can control the X-ray source and the detector to move to a position aligned with the region of interest.

Next, in 340, the controller can further determine the size of the region of interest and a quantity to be stitched.

In some embodiments, the controller can determine the size of the region of interest based on an image capture site of the subject under examination. For example, if the image capture site of the subject under examination is the shoulders and neck, the controller can roughly determine the size of the region of interest and determine the quantity of images to be stitched based on the size of the detector and the size of an overlapping region needed for the stitching. The size of the overlapping region needed for the stitching means that if two images need to be stitched, at least a part (for example, a distance of 7 cm) of the two images needs to be overlapped, so that there is an overlapping part between the two images, which is necessary for implementing image stitching.

In some other embodiments, the controller can determine a region of interest in a camera image acquired by the camera based on the camera image. FIG. 5 shows a schematic diagram of a region of interest 301 according to some embodiments of the present invention. As shown in FIG. 5, a camera image of the subject under examination acquired based on the camera unit 140 in FIG. 1 is displayed or shown in a user interface of a display unit. In addition, the region of interest can be further displayed on the user interface. A user or an operator of the X-ray imaging system may input or select, through the user interface, the region of interest of the subject under examination for imaging. As a non-limiting example, the region of interest may include the entire shoulders and neck, pelvis, hip joint, and the like of the subject under examination. Certainly, the controller can also automatically identify the region of interest and position of the subject under examination based on identification of a key point of the subject under examination.

In some embodiments, a stitching start position of the X-ray source does not necessarily have to be determined by moving the X-ray source to the center of the region of interest. Instead, a start position and an end position of the X-ray source can be determined by determining a boundary region of a stitching region. For example, using imaging the shoulders and neck as an example, the outermost side of the left shoulder (or the right shoulder) may be used as the stitching start position and the outermost side of the right shoulder (or the left shoulder) may be used as the stitching end position. By determining the start position and the end position, the quantity of images to be stitched can be determined based on the start position and the end position, and the X-ray source can then be controlled to rotate or move to emit X-rays.

Next, in 350, the controller can further control the X-ray source to acquire the first quantity of X-ray images by rotation or translation.

Specifically, in some embodiments, the controller is further configured to control the X-ray source to emit X-rays at a plurality of different angles, respectively, to acquire the first quantity of X-ray images.

Specifically, the controller is further configured to rotate the X-ray source along the width direction of the examination table to a first angle through an $n^{th}$ angle to align with a first part to an $n^{th}$ part of the region of interest, so as to acquire a first X-ray image to an $n^{th}$ X-ray image of the subject under examination, and stitch the first X-ray image to the $n^{th}$ X-ray image to acquire a panoramic image of the subject under examination, where n is the first quantity. Specifically, the X-ray source can rotate in the vertical plane, so that the X-ray source can different positions along the width direction of the examination table.

Specifically, for example, the first quantity is 2. The region of interest can be divided into a first part and a second part based on the size of the detector and the size of an overlapping region of images to be stitched. The first part and the second part have an overlapping part. The controller is further configured to rotate the X-ray source to the first angle to align with the first part of the region of interest, so as to acquire the first X-ray image of the subject under examination; rotate the X-ray source to a second angle to align with the second part of the region of interest to acquire a second X-ray image of the subject under examination; and stitch the first X-ray image and the second X-ray image to acquire the panoramic image of the subject under examination. Certainly, when the first quantity is greater than 2, the controller can further rotate the X-ray source to a third angle to align with a third part of the region of interest and stitch the acquired three X-ray images.

In some other embodiments, the controller is further configured to control the X-ray source to emit X-rays (360) at a plurality of different positions, respectively, to acquire the first quantity of X-ray images, i.e. to move the X-ray source along the width direction of the examination table, so that the X-ray source is aligned with the central positions of different parts of the region of interest, respectively.

Specifically, the controller is further configured to move the X-ray source to a first position through an $n^{th}$ position to align with a first part to an $n^{th}$ part of the region of interest, so as to acquire a first X-ray image to an $n^{th}$ X-ray image of the subject under examination, and stitch the first X-ray image to the $n^{th}$ X-ray image to acquire a panoramic image of the subject under examination, where n is the first quantity.

For example, the first quantity is 2. The region of interest can be divided into a first part and a second part based on the size of the detector and the size of an overlapping region of images to be stitched. The controller is further configured to: move the X-ray source to the first position to align with the first part of the region of interest, so as to acquire the first X-ray image of the subject under examination; move the X-ray source to a second position to align with the second part of the region of interest to acquire a second X-ray image of the subject under examination; and stitch the first X-ray image and the second X-ray image to acquire the panoramic image of the subject under examination.

Finally, in 360, the controller can be further configured to perform image stitching on the acquired first quantity of X-ray images. Specifically, a conventional mechanism for automatically stitching two overlapping images together may include a search-based method, in which common anatomical features between the overlapping images are identified and used as the basis for stitching the images. Certainly, it is also possible to perform image stitching based on, for example, a depth learning model. Any suitable manner may be used for image stitching, and no limitation is imposed herein.

Figure 6:
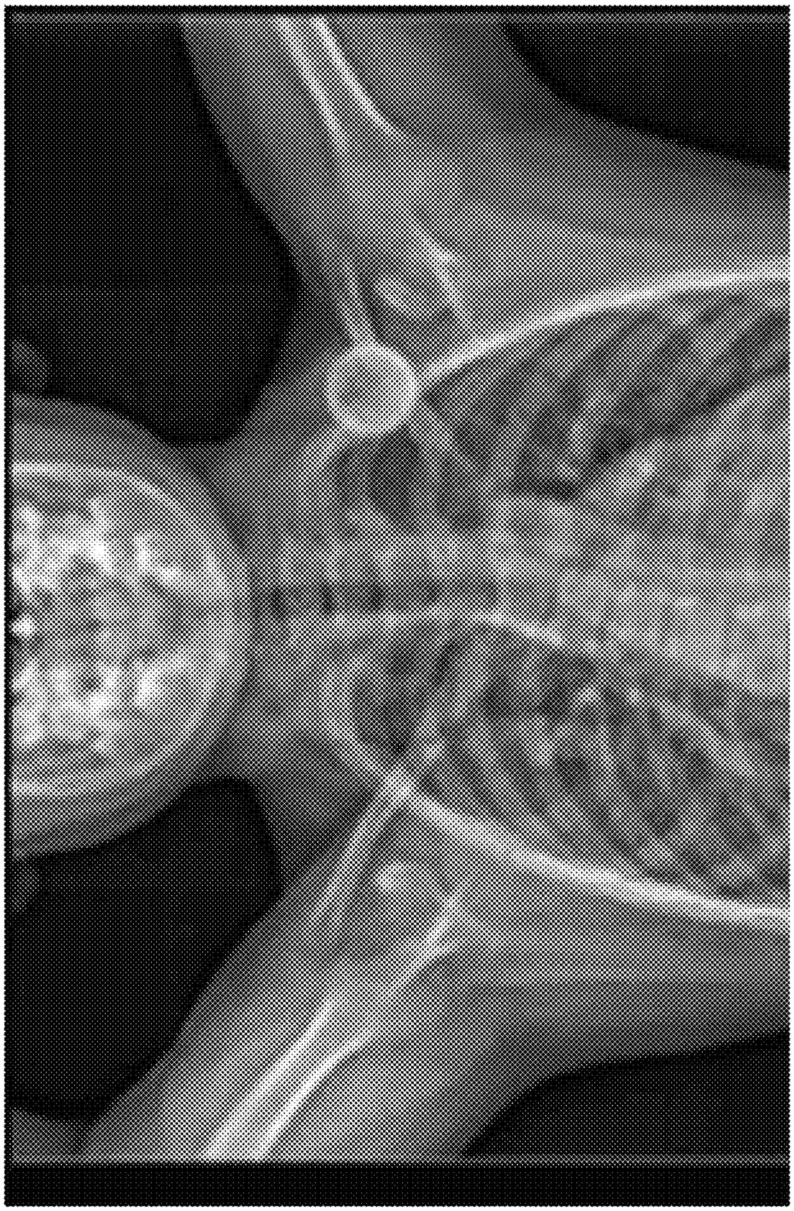
FIG. 6 is a schematic diagram of a panoramic image acquired according to some embodiments of the present invention.

FIG. 6 is a schematic diagram of a panoramic image acquired according to some embodiments of the present invention. As shown in FIG. 6, the panoramic image obtained along the width direction of the human body can display the left and right shoulders and neck of the subject under examination, facilitating comparison and diagnosis by a user or an operator.

In some embodiments, the controller can be further configured to control the motion of the X-ray source and the detector to acquire a second quantity of X-ray images of the subject under examination along the length direction of the examination table, and can perform image stitching on the second quantity of X-ray images and the panoramic image in the width direction to acquire a whole-body image of the subject under examination. Specifically, an image of the spine or a panoramic image of the legs of the subject under examination may be acquired along the length direction of the examination table. By acquiring a plurality of images along the length direction of the examination table, images of the subject under examination, e.g., images from the head to feet, can be acquired along the height of the subject under examination. Additionally, the whole-body image of the subject under examination can be acquired by combining the panoramic images of the subject under examination at different angles may be acquired along the length direction and the width direction of the examination table.

Although the X-ray imaging system is a suspended X-ray imaging system in the above description, certainly, the current image stitching method and apparatus may also be applied to a ground rail-type X-ray imaging system and a mobile X-ray imaging system. Specifically, the X-ray source may be mounted on a ground rail-type cross arm, that is, the cross arm on which the X-ray source is mounted is mounted in a rail on the ground via a wall stand, and the X-ray source can carry out motion along the rail, the wall stand, and the cross arm. Certainly, the X-ray source may alternatively be mounted on a mobile cart via a telescopic arm.

Figure 7:
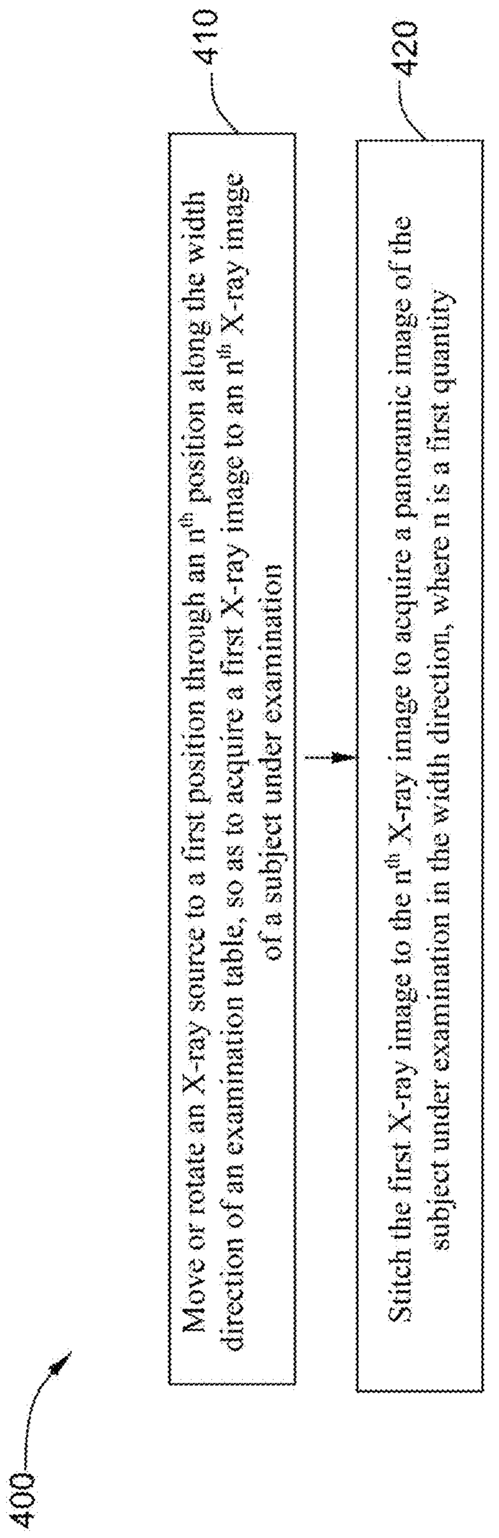
FIG. 7 is a flowchart of an X-ray imaging method according to some embodiments of the present invention.

FIG. 7 is a flowchart of an X-ray imaging method according to some embodiments of the present invention. As shown in FIG. 7, an X-ray imaging method 400 includes step 410, step 420, and step 430.

In step 410, an X-ray source is moved or rotated to a first position through an $n^{th}$ position along the width direction of an examination table, so as to acquire a first X-ray image to an $n^{th}$ X-ray image of a subject under examination.

In some embodiments, before step 410, the X-ray imaging method further includes: controlling a suspension apparatus and a detector to move such that the X-ray source and the detector are aligned with the center of a region of interest of the subject under examination. Specifically, the controlling a suspension apparatus to move such that the X-ray source and the detector are aligned with the center of a region of interest of the subject under examination includes automatically controlling the suspension apparatus and the detector to move to a target position based on a position of a handheld positioning apparatus. In some other embodiments, the controlling a suspension apparatus to move such that the X-ray source and the detector are aligned with the center of a region of interest of the subject under examination includes: determining the center of the region of interest based on the camera images of the subject under examination acquired by a camera, based on identification of a key point, or based on an image capture site of the subject under examination or an input or selection by a user, and then automatically moving the X-ray source and the detector to align with the center of the region of interest in the camera based on the positional related between the camera and the X-ray source.

In some embodiments, step 410 further includes: rotating the X-ray source along the width direction of the examination table to a first angle through an $n^{th}$ angle to align with a first part to an $n^{th}$ part of the region of interest, so as to acquire a first X-ray image to an $n^{th}$ X-ray image of the subject under examination, and stitch the first X-ray image to the $n^{th}$ X-ray image to acquire a panoramic image of the subject under examination, where n is a first quantity.

In some other embodiments, step 410 further includes: moving the X-ray source to a first position through an $n^{th}$ position to align with a first part to an $n^{th}$ part of the region of interest, so as to acquire a first X-ray image to an $n^{th}$ X-ray image of the subject under examination, and stitch the first X-ray image to the $n^{th}$ X-ray image to acquire a panoramic image of the subject under examination, where n is a first quantity.

In step 420, the first X-ray image to the $n^{th}$ X-ray image are stitched to acquire a panoramic image of the subject under examination in the width direction, where n is the first quantity.

Specifically, a conventional mechanism for automatically stitching two overlapping images together may include a search-based method, in which common anatomical features between the overlapping images are identified and used as the basis for stitching the images. Certainly, it is also possible to perform image stitching based on, for example, a depth learning model.

Figure 8:
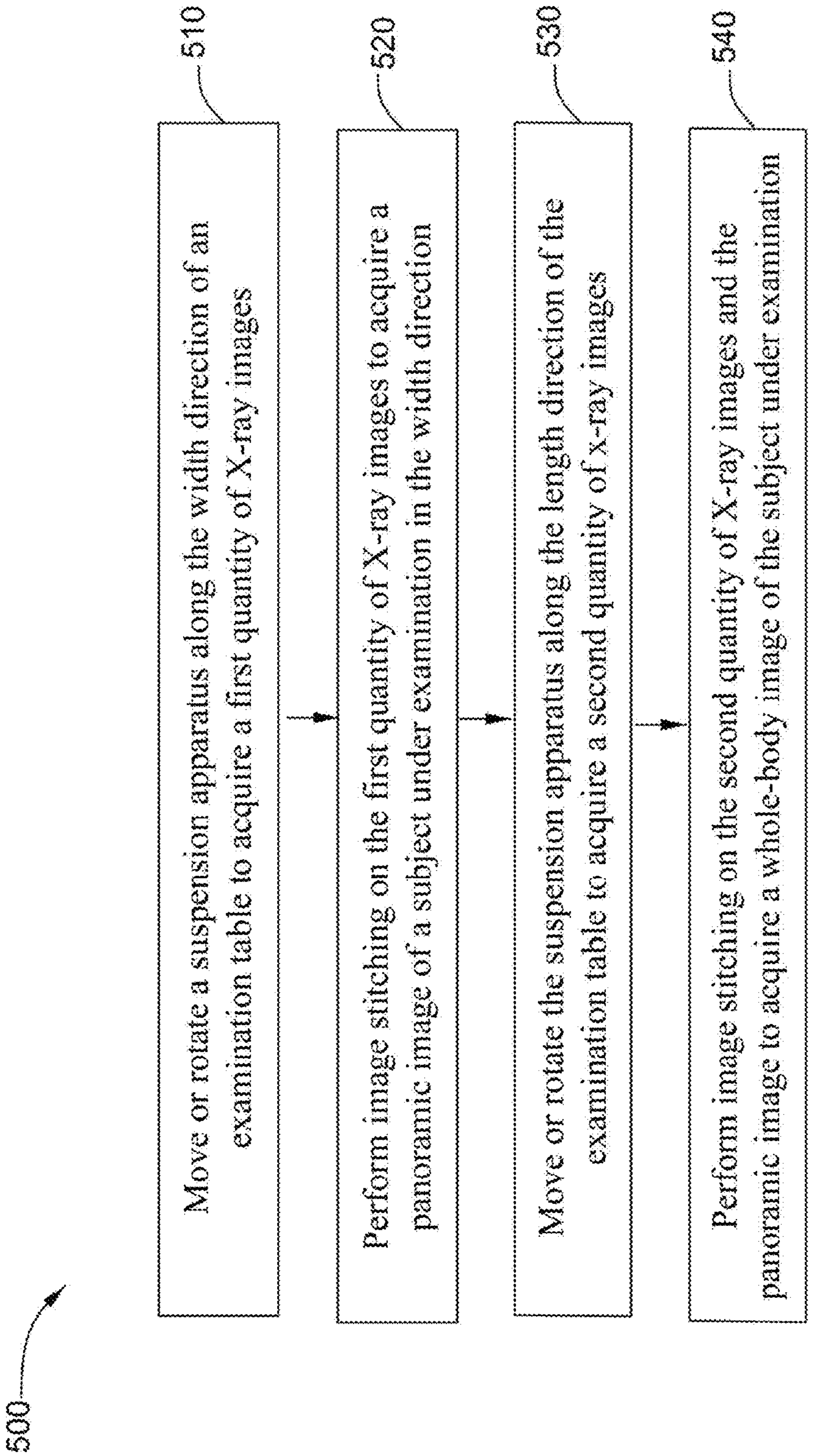
FIG. 8 is a flowchart of an X-ray imaging method according to some other embodiments of the present invention.

FIG. 8 is a flowchart of an X-ray imaging method according to some other embodiments of the present invention. As shown in FIG. 8, an X-ray imaging method 500 includes step 510, step 520, step 530, and step 540.

In step 510, an X-ray source is moved or rotated along the width direction of an examination table to acquire a first quantity of X-ray images.

In step 520, image stitching is performed on the first quantity of X-ray images to acquire a panoramic image of the subject under examination in the width direction.

In step 530, the X-ray source is moved or rotated along the length direction of the examination table to acquire a second quantity of X-ray images. Specifically, the second quantity is any integer greater than 1, for example, may be 2, 3, or any more.

In step 540, image stitching is performed on the second quantity of X-ray images and the panoramic image to acquire a whole-body image of the subject under examination.

According to the X-ray imaging system and method of some embodiments of the present invention, firstly, a detector capable of moving along the length direction and the width direction of an examination table is provided, and an X-ray source is rotated or translated along the width direction of the examination table. In this way, a plurality of X-ray images can be acquired along the width direction of the examination table and then stitched to obtain a panoramic image of a human body in the width direction, so that the similar shoulders and neck on both sides can be displayed in the same image, facilitating judgment or diagnosis by doctors. In addition, by acquiring a plurality of X-ray images along each of the width direction and the length direction of the examination table, it is possible to acquire the whole-body image of the subject under examination by stitching.

The exemplary embodiments of the present invention further provide an X-ray imaging system. The X-ray imaging system includes an examination table, an X-ray source, and a controller. A detector is mounted inside the examination table, and the detector can carry out motion along the length direction and the width direction of the examination table. The X-ray source and the detector can cooperate to acquire an X-ray image of a subject under examination. The controller can control motion of the X-ray source and the detector to acquire a first quantity of X-ray images of the subject under examination along the width direction of the examination table, and can perform image stitching on the first quantity of X-ray images to acquire a panoramic image of the subject under examination in the width direction.

Specifically, the controller can be further configured to control the X-ray source to move such that the X-ray source is aligned with the center of a region of interest of the subject under examination.

Specifically, the controller is further configured to acquire the region of interest.

Specifically, the controller can be further configured to: rotate the X-ray source to a first angle through an $n^{th}$ angle to align with a first part to an $n^{th}$ part of the region of interest, so as to acquire a first X-ray image to an $n^{th}$ X-ray image of the subject under examination; and stitch the first X-ray image to the $n^{th}$ X-ray image to acquire a panoramic image of the subject under examination, where n is the first quantity.

Specifically, the X-ray source is mounted on a suspension apparatus, and the suspension apparatus further includes a tube console, and before rotating the X-ray source to the first angle, the controller can be further configured to control the suspension apparatus to rotate in a horizontal plane such that a reference line is parallel to the length direction of the examination table, where the reference line is a direction perpendicular to a screen plane of the tube console.

Specifically, the controller can be further configured to move the X-ray source to a first position through an $n^{th}$ position to align with a first part to an $n^{th}$ part of the region of interest, so as to acquire a first X-ray image to an $n^{th}$ X-ray image of the subject under examination; and stitch the first X-ray image to the $n^{th}$ X-ray image to acquire a panoramic image of the subject under examination, where n is the first quantity.

Specifically, the controller can be further configured to control the motion of the X-ray source and the detector to acquire a second quantity of X-ray images of the subject under examination along the length direction of the examination table, and can perform image stitching on the second quantity of X-ray images and the panoramic image in the width direction to acquire a whole-body image of the subject under examination.

The exemplary embodiments of the present invention further provide an X-ray imaging method. The X-ray imaging method includes: moving or rotating an X-ray source to a first position through an $n^{th}$ position along the width direction of an examination table, so as to acquire a first X-ray image to an $n^{th}$ X-ray image of a subject under examination; and stitching the first X-ray image to the $n^{th}$ X-ray image to acquire a panoramic image of the subject under examination in the width direction, where n is a first quantity.

The exemplary embodiments of the present invention further provide an X-ray imaging method. The X-ray imaging method includes: moving or rotating an X-ray source along the width direction of an examination table to acquire a first quantity of X-ray images; performing image stitching on the first quantity of X-ray images to acquire a panoramic image of a subject under examination in the width direction; moving or rotating the X-ray source along the length direction of the examination table to acquire a second quantity of X-ray images; performing image stitching on the second quantity of X-ray images and the panoramic image to acquire a whole-body image of the subject under examination.

As used herein, the term "computer" may include any processor-based or microprocessor-based system, including a system using a microcontrol apparatus, a reduced instruction set computer (RISC), an application-specific integrated circuit (ASIC), a logic circuit, and any other circuit or processor capable of performing the functions described herein. The examples above are exemplary only and are not intended to limit the definition and/or meaning of the term "computer" in any way.

Some exemplary embodiments have been described above; however, it should be understood that various modifications may be made. For example, suitable results can be achieved if the described techniques are performed in a different order and/or if components in the described systems, architectures, devices, or circuits are combined in different ways and/or replaced or supplemented by additional components or equivalents thereof. Accordingly, other implementations also fall within the scope of protection of the claims.

The invention claimed is:

1. An X-ray imaging system, comprising:

an examination table, wherein a detector is mounted inside the examination table, and the detector is capable of carrying out motion along the length direction and the width direction of the examination table;

an X-ray source, wherein the X-ray source and the detector are capable of cooperation to acquire an X-ray image of a subject under examination; and a controller, wherein the controller is capable of controlling motion of the X-ray source and the detector to acquire a first quantity of X-ray images of the subject under examination along the width direction of the examination table, and is capable of performing image stitching on the first quantity of X-ray images to acquire a panoramic image of the subject under examination in the width direction, wherein the X-ray imaging system further comprises a camera unit aligned with the detector and configured to acquire real-time camera images and depth information of the subject, and wherein the controller is further configured to control motion of the X-ray source and the detector based on the real-time camera images and the depth information.

2. The X-ray imaging system according to claim 1, wherein the controller is capable of being further configured to control the X-ray source to move such that the X-ray source is aligned with the center of a region of interest of the subject under examination.

3. The X-ray imaging system according to claim 2, wherein the controller is further configured to acquire the region of interest.

4. The X-ray imaging system according to claim 2, wherein the controller is further configured to rotate the X-ray source to a first angle through an $n^{th}$ angle to align with a first part to an $n^{th}$ part of the region of interest, so as to acquire a first X-ray image to an $n^{th}$ X-ray image of the subject under examination.

5. The X-ray imaging system according to claim 4, wherein the controller is further configured to stitch the first X-ray image to the $n^{th}$ X-ray image to acquire a panoramic image of the subject under examination, wherein n is the first quantity.

6. The X-ray imaging system according to claim 5, wherein the X-ray source is mounted on a suspension apparatus, and the suspension apparatus includes a tube console, and before rotating the X-ray source to the first angle, the controller is configured to control the suspension apparatus to rotate in a horizontal plane such that a reference line is parallel to the length direction of the examination table, wherein the reference line is a direction perpendicular to a screen plane of the tube console.

7. The X-ray imaging system according to claim 2, wherein the controller is further configured to move the X-ray source to a first position through an $n^{th}$ position to align with a first part to an $n^{th}$ part of the region of interest, so as to acquire a first X-ray image to an $n^{th}$ X-ray image of the subject under examination.

8. The X-ray imaging system according to claim 7, wherein the controller is further configured to stitch the first X-ray image to the $n^{th}$ X-ray image to acquire a panoramic image of the subject under examination, wherein n is the first quantity.

9. The X-ray imaging system according to claim 1, wherein the controller is capable of being further configured to control the motion of the X-ray source and the detector to acquire a second quantity of X-ray images of the subject under examination along the length direction of the examination table, and is capable of performing image stitching on the second quantity of X-ray images and the panoramic image in the width direction to acquire a whole-body image of the subject under examination.

10. The X-ray imaging system according to claim 1, wherein the camera unit is mounted on a suspension apparatus of the X-ray imaging system.

11. The X-ray imaging system according to claim 1, wherein the camera unit is configured to acquire the depth information based on a three-dimensional point cloud of the subject under examination.

12. The X-ray imaging system according to claim 1, wherein the camera unit comprises at least one of a depth camera, an infrared camera, a 3D camera, a 3D scanner, or an RGB-D sensor.

13. The X-ray imaging system according to claim 1, wherein the camera unit comprises a control module configured to control rotation of the camera unit to adjust a capture range.

14. The X-ray imaging system according to claim 1, wherein the controller is further configured to select, from a plurality of detectors, the detector to be used for image acquisition based on at least one of a detected position or a pose of the subject determined from the real-time camera images.

15. The X-ray imaging system according to claim 1, further comprising a beam limiter configured to define an exposure field of view corresponding to a region of interest of the subject under examination.

16. The X-ray imaging system according to claim 1, wherein the X-ray source is configured to rotate in both a vertical plane and a horizontal plane.

17. The X-ray imaging system according to claim 1, wherein the controller is further configured to determine at least one of thickness, height, position, or pose of the subject based on the real-time camera images and the depth information.

18. An X-ray imaging method, comprising:

moving or rotating an X-ray source to a first position through an $n^{th}$ position along the width direction of an examination table, so as to acquire a first X-ray image to an $n^{th}$ X-ray image of a subject under examination, wherein moving or rotating the X-ray source comprises acquiring, using a camera unit aligned with a detector, real-time camera images and depth information of the subject under examination and controlling motion of the X-ray source based on the real-time camera images and the depth information; and stitching the first X-ray image to the nth X-ray image to acquire a panoramic image of the subject under examination in the width direction, wherein n is a first quantity.

19. The X-ray imaging method according to claim 18, further comprising controlling the X-ray source and the detector to move such that the X-ray source and the detector are aligned with the center of a region of interest of the subject under examination.

20. An X-ray imaging method, comprising:

moving or rotating an X-ray source along the width direction of an examination table to acquire a first quantity of X-ray images;

performing image stitching on the first quantity of X-ray images to acquire a panoramic image of a subject under examination in the width direction;

moving or rotating the X-ray source along the length direction of the examination table to acquire a second quantity of X-ray images, wherein moving or rotating the X-ray source comprises acquiring, using a camera unit aligned with a detector, real-time camera images and depth information of the subject under examination and controlling motion of the X-ray source based on the real-time camera images and the depth information; and performing image stitching on the second quantity of X-ray images and the panoramic image to acquire a whole-body image of the subject under examination.

* * * * *